.

US010696963B2

(12) United States Patent
Daley et al.

(10) Patent No.: US 10,696,963 B2
(45) Date of Patent: Jun. 30, 2020

(54) SELECTIVE OPTIMIZATION OF A RIBOSOME BINDING SITE FOR PROTEIN PRODUCTION

(71) Applicant: CloneOpt AB, Upplands Väsby (SE)

(72) Inventors: Daniel Daley, Upplands Väsby (SE);
Kiavash Mirzadeh, Järfälla (SE);
Stephen Toddo, Hägersten (SE);
Suchithra Guntur, Brampton (CA)

(73) Assignee: CloneOpt AB, Upplands Vasby (SE)

( * ) Notice: Subject to any disclaimer, the term of this patent is extended or adjusted under 35 U.S.C. 154(b) by 505 days.

(21) Appl. No.: 15/535,686

(22) PCT Filed: Dec. 15, 2015

(86) PCT No.: PCT/SE2015/051343
§ 371 (c)(1),
(2) Date: Jun. 13, 2017

(87) PCT Pub. No.: WO2016/099388
PCT Pub. Date: Jun. 23, 2016

(65) Prior Publication Data
US 2018/0273934 A1 Sep. 27, 2018

(30) Foreign Application Priority Data
Dec. 16, 2014 (SE) ...................................... 1451553

(51) Int. Cl.
C12N 15/10 (2006.01)
C12N 15/67 (2006.01)
(52) U.S. Cl.
CPC ......... *C12N 15/1086* (2013.01); *C12N 15/67* (2013.01)
(58) Field of Classification Search
None
See application file for complete search history.

(56) References Cited

U.S. PATENT DOCUMENTS

2003/0114650 A1* 6/2003 Cheung .................. C07K 14/31
536/23.1

FOREIGN PATENT DOCUMENTS

WO WO 2009/112587 9/2009

OTHER PUBLICATIONS

Bucheler et al (Nucleic Acids Research 20:3127-33) (Year: 1992).*
Cheong et al., "Enhancing functional expression of heterologous proteins through random substitution of genetic codes in the 5' coding region," Biotechnology and Bioengineering., Apr. 2015, 112 (4): 822-826.
Daley et al., "Global topology analysis of the *Escherichia coli* inner membrane proteome," Science, 2005, 308: 1321-1323.
Dvir et al., "Deciphering the rules by which 5'-UTR sequences affect protein expression in yeast," PNAS, 2013, 110: E2792-2801.
Goltermann et al., "Tuning protein expression using synonymous codon libraries targeted to the 5' mRNA coding region," Protein Engineering, Design & Selection, 2011, 24(1-2): 123-129.
Hui et al., "Mutagenesis of the three bases preceding the start codon of the beta-galactosidase mRNA and its effect on translation in *Escherichia coli*," The EMBO Journal, 1984, 3: 623-629.
International Search Report and Written Opinion in International Application No. PCT/SE2015/051343, dated Mar. 29, 2016, 13 pages.
Kudla et al., "Coding-sequence determinants of gene expression in *Escherichia coli*," Science, 2009, 324: 255-258.
Liebeton et al., "The nucleotide composition of the spacer sequence influences the expression yield of heterologously expressed genes in Bacillus subtilis", J of Biothech, Jul. 2014, 191: 214-220.
Looman et al., "Influence of the codon following the AUG initiation codon on the expression of a modified lacZ gene in *Escherichia coli*," The EMBO Journal, 1987, 6: 2489-2492.
Matteucci et al., "Targeted random mutagenesis: the use of ambiguously synthesized oligonucleotides to mutagenize sequences immediately 5' of an ATG initiation codon.," Nucleic Acids Research, May 1983, 11(10):3113-3121.
Mirzadeh et al. "Enhanced Protein Production in *Escherichia coli* by Optimization of Cloning Scars at the Vector-Coding Sequence Junction", ACS Synthetic Biology, Sep. 2015, 4(9): 959-965.
Mirzadeh et al. "Codon optimizing for increased membrane protein production: a minimalist approach," Heterologous Expression of Membrane Proteins: Methods and Protocols, Chapter 4, Springer, 2016, 53-61.
Mutalik et al., "Quantitative estimation of activity and quality for collections of functional genetic elements," Nature Methods, 2013, 10:347-353.
Na et al., "Mathematical modeling of translation initiation for the estimation of its efficiency to computationally design mRNA sequences with desired expression levels in prokaryotes," BMC Systems Biology, 2010, 4:71 (16 pages).
Norholm et al., "Improved production of membrane proteins in *Escherichia coli* by selective codon substitutions", FEBS Letters, Jun. 2013, 587(15): 2352-2358.

(Continued)

*Primary Examiner* — Christopher M Gross
(74) *Attorney, Agent, or Firm* — Fish & Richardson P.C.

(57) ABSTRACT

A method for optimising a nucleotide sequence for protein expression in a host cell, comprising the steps of: (a) constructing an expression library comprising a large number of variants of the sequence to be expressed operatively cloned in an expression vector, wherein (i) the sequence of the 6 nucleotides immediately upstream (5'-direction) of the first codon of the coding sequence to be expressed is completely or partially randomized; (ii) the sequence of the second and third codons of the coding sequence to be expressed is randomized, wherein the randomization of the second and third codons is limited to changes not altering the amino-acids encoded by said codons; (b) screening the library with regard to efficiency of protein expression in the host cell; and (c) selecting a sequence resulting in a desired level of efficiency of protein expression.

30 Claims, 10 Drawing Sheets
Specification includes a Sequence Listing.

(56) References Cited

OTHER PUBLICATIONS

Salis et al., "Automated design of synthetic ribosome binding sites to control protein expression," Nature Biotechnology, 2009, 27: 946-950.

Schaerli et al., "Building synthetic gene circuits from combinational libraries: screening and selection strategies," Mol. BioSyst., 2013, 9,:1559-1567.

Seo et al., "Predictive design of mRNA translation initiation region to control prokaryotic translation efficiency", Metabolic Engineering, Jan. 2013, 15:67-74.

Stenstrom et al., "Cooperative effects by the initiation codon and its flanking regions on translation initiation," Gene, Aug. 2001, 273(2): 259-265.

Stenstrom et al., "Codon bias at the 3'-side of the initiation codon is correlated with translation initiation efficiency in *Escherichia coli*," Gene, 2001, 263: 273-284.

Toddo, "Engineering membrane proteins for production and topology" Thesis at Stockholm University, 2015, 112 pages.

Vize et al., "Spacer alterations which increase the expression of porcine growth hormone in *E. coli*," Department of Biochemistry, University of Adelaide, Mar. 1987, 213(1):155-158.

\* cited by examiner

SEQUENCE LISTING

```
<160> NUMBER OF SEQ ID NOS: 3

<210> SEQ ID NO 1
<211> LENGTH: 50
<212> TYPE: DNA
<213> ORGANISM: Artificial
<220> FEATURE:
<223> OTHER INFORMATION: Synthetic primer

<400> SEQUENCE: 1
tctccttctt aaagttaaac aaaattattc tagaggggaa ttgttatccg            50

<210> SEQ ID NO 2
<211> LENGTH: 23
<212> TYPE: DNA
<213> ORGANISM: Artificial
<220> FEATURE:
<223> OTHER INFORMATION: Artificial vector:CDS junction

<400> SEQUENCE: 2
tttaagaagg agactcgagg atg                                         23

<210> SEQ ID NO 3
<211> LENGTH: 20
<212> TYPE: DNA
<213> ORGANISM: Artificial
<220> FEATURE:
<223> OTHER INFORMATION: Artificial vector:CDS junction
<220> FEATURE:
<221> NAME/KEY: misc_feature
```

```
<222> LOCATION: (12)..(17)
<223> OTHER INFORMATION: n is a, c, g, or t

<400> SEQUENCE: 3
aagaaggaga cnnnnnnatg                                                     20
```

SELECTIVE OPTIMIZATION OF A RIBOSOME BINDING SITE FOR PROTEIN PRODUCTION

CROSS-REFERENCE TO RELATED APPLICATIONS

This application is a National Stage application under 35 U.S.C. § 371 of International Application No. PCT/SE2015/051343, having an International Filing Date of Dec. 15, 2015, which claims the benefit of Sweden Application Serial No. 1451553-0 filed Dec. 16, 2014. This disclosures of each of these prior applications are incorporated by reference herein in their entireties.

TECHNICAL FIELD

The present invention relates to the field of DNA constructs for recombinant protein expression.

BACKGROUND TO THE INVENTION

Protein production in *Escherichia coli* is a fundamental activity for a large fraction of academic, pharmaceutical and industrial research laboratories. Maximum production levels are usually sought, as this reduces costs and facilitates downstream purification steps.

A rate-limiting step in protein synthesis is translation initiation. In this process the ribosome must bind to the mRNA at a region called the Ribosome Binding Site (RBS). The RBS is approximately 35 nucleotides long and contains three discrete domains; (1) the Shine-Dalgarno (SD) sequence, (2) a spacer region, and (3) the first five to six codons of the Coding Sequence (CDS) (FIG. 1).

To enable maximum production levels, coding sequences (CDSs) to be expressed recombinantly are typically cloned into high-copy number vectors that contain optimised genetic elements, such as promoters selected for high-level transcription and Shine-Dalgarno sequences selected for efficient translation.

When a CDS is cloned into an expression vector, the natural 5' untranslated region (UTR) is typically replaced by a vector-derived 5'UTR and a new RBS is formed. The nature of this RBS is dictated by the newly formed junction between the vector and the CDS. Thus a vector that works for one coding sequence might not work for another[1,2]. This problem is known as context dependence and it results in unpredictable expression levels.

It has been noted that nucleotide changes in the RBS can modulate protein production. Prior art in this area include a number of studies that have noted that nucleotide changes in the spacer[3,4] can have an influence on protein production. It has also been noted that nucleotide changes in the 5'-end of the CDS can have an influence on protein production[5-9]. Moreover, there is also a body of work that shows that inserting domains into the RBS can influence the levels of protein production. Whilst these studies demonstrate how nucleotide changes in the RBS affect protein production, they do not solve the problem of context dependence, because they do not consider the vector and the CDS at the same time.

The best available tool for designing an optimal RBS is the RBS-calculator[2]. This calculator is a prediction tool that uses a thermodynamic model of translational initiation (i.e. free-energy or ΔG calculations) to design a SD and linker region that is most optimal for maximum production of the CDS of interest. It therefore considers context. However, the calculator is based on a bioinformatics prediction and its reliability is calculated to be around 47% (within 2-two-fold of a target expression level). The calculator does not consider synonymous codon choice in the 5'end of the CDS.

The method disclosed in WO2009112587A3, like the RBS calculator, matches a SD and linker region with a CDS of interest. The described solution uses a two-step cloning approach that modulates the nucleotide sequence of the SD and the linker, but not the CDS. The increases in protein production observed are however marginal compared to those observed with the present method.

The problem of unpredictable and often undesirably low expression level is of fundamental nature and has been recognized already in the early days of molecular biology, but a general experimental solution has not been presented. Therefore, an object of the present invention is to provide an improved experimental method for optimizing the RBS of a DNA construct for recombinant protein expression.

Definitions

The term Shine-Dalgarno sequence (SD) refers to is a ribosomal binding site in prokaryotic mRNA, generally located around 8 bases upstream of the start codon AUG. It may also refer to corresponding sequence in a DNA polynucleotide being a potential template for an mRNA. In *E. coli*, the SD consensus sequence is AGGAGGU, while an example of a specific sequence optimized for expression is AAGAAGGA.

The term spacer region refers to the stretch of about 8 nucleotides in prokaryotic mRNA located between the SD and the coding sequence of the mRNA. It may also refer to corresponding sequence in a DNA polynucleotide being a potential template an mRNA.

The term Ribosomal Binding Site (RBS) refers to a sequence on mRNA that the ribosome binds to when initiating protein translation. The RBS is approximately 35 nucleotides long and contains three discrete domains; (1) the Shine-Dalgarno (SD) sequence, (2) a spacer region, and (3) the first five to six codons of the Coding Sequence (CDS) (FIG. 1). It may also refer to corresponding sequence in a DNA polynucleotide being a potential template for an mRNA.

The term "degenerate primers" or "a set of degenerate primers" refers to a collection of primers that share certain identical sequence elements, but where certain sequence elements differ between the individual primers by design.

SUMMARY OF THE INVENTION

Figure 1:
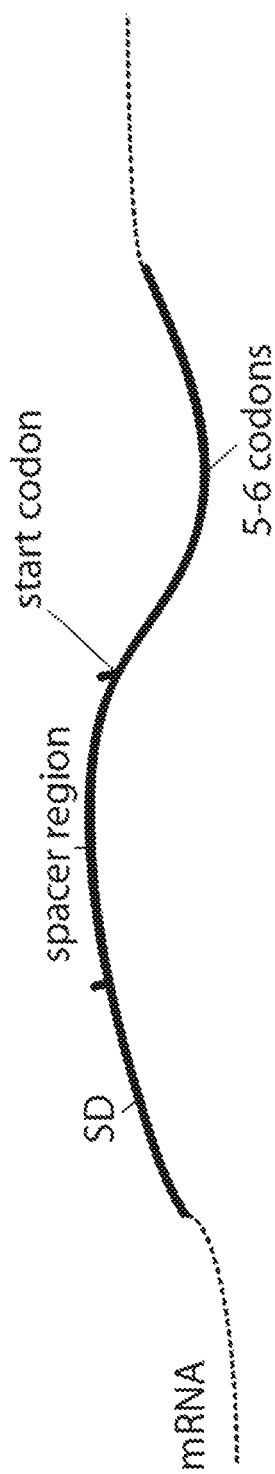
FIG. 1. The RBS contains three discrete domains.

The present invention provides simple methods to generate and identify RBS-variants that give an improved level of expression. The method is preferably PCR-based and uses a set of degenerate primers to randomise the 6 nucleotides on either side of the triplet encoding the AUG start codon (without changing the encoded amino acid sequence). The approach therefore randomises the junction between the vector and the coding sequence in a constrained manner. Typically, the method will generate a library of a large number of clones that vary at the vector: coding sequence junction. When transcribed, the mRNA will have different RBSs. Optimum variants can be selected by screening for high expressing clones. The method has been tested on a wide range of different CDSs with remarkable results. For example, coding sequences that were previously thought to be difficult-to-express could be expressed at levels >60 mg/L after been engineered using this approach. The invention provides a simple and inexpensive solution to increasing protein production.

The present invention relates to the following items. The subject matter disclosed in the items below should be regarded disclosed in the same manner as if the subject matter were disclosed in patent claims.

1. A method for optimising a nucleotide sequence for protein expression in a host cell, comprising the steps of:
   a. constructing an expression library comprising a large number of variants of the sequence to be expressed operatively cloned in an expression vector, wherein
      i. the sequence of the 6 nucleotides immediately upstream of the sequence of the first codon of the coding sequence to be expressed is completely or partially randomized;
      ii. the sequence of the second and third codons of the coding sequence to be expressed is randomized, wherein the randomization of the second and third codons is limited to changes not altering the amino-acids encoded by said codons;
   b. screening the library with regard to efficiency of protein expression in the host cell; and
   c. selecting a sequence resulting in a desired level of efficiency of protein expression.

2. The method according to any of the preceding items, wherein construction step (a) comprises a PCR reaction involving a set of degenerate primers comprising:
   (i) a sequence of least 6 completely or partially randomised nucleotides in 5'-direction of the first codon of the sequence to be expressed;
   (ii) the sequence encoding the first codon of the sequence to be expressed; and
   (iii) a partially randomized sequence of the second and third codons of the sequence to be expressed, wherein the randomization of the sequence of the second and third codons is limited to changes not altering the amino-acids encoded by said codons; or the complement of said sequences in (i)-(iii).
3. The method according to any of the preceding items, wherein the library is designed to comprise at least 1000 variants of the 6 nucleotides in 5'-direction of the first codon of the sequence to be expressed.
4. The method according to any of the preceding items, wherein the library is designed to comprise at least 2 variants of the sequence of the second and third codons.
5. The method according to any of the preceding items, wherein the library is designed to comprise at least 4000 variants of the nucleotide sequence to be optimised.
6. The method according to any of the preceding items, wherein the operative cloning in an expression vector results, when introduced into a suitable host under suitable conditions, in expression of an mRNA molecule comprising at least the following features, in the following order from the 5' direction: (i) the sequence of the 6 nucleotides immediately in 5'-direction of the first codon of the coding sequence to be expressed and (ii) the coding sequence to be expressed.
7. The method according to any of the preceding items, wherein the operative cloning in an expression vector results, when introduced into a suitable host under suitable conditions, in expression of an mRNA molecule comprising at least the following features, in the following order from the 5' direction: (i) a Shine-Dalgarno sequence (ii) the sequence of the 6 nucleotides immediately in 5'-direction of the first codon of the coding sequence to be expressed and (iii) the coding sequence to be expressed.
8. The method according to any of the preceding items, wherein the library is constructed such that the sequence be expressed is expressed as a fusion protein with a detectable marker.
9. The method according to item 8, wherein the detectable marker is a fluorescent protein.
10. The method according to item 9, wherein the screening step is performed by flow cytometry.
11. The method according to any of the preceding items, wherein the expression vector comprises a Shine-Dalgarno sequence.
12. The method according to any of the preceding items, wherein the expression vector is a high copy number vector.
13. The method according to any of the preceding items, wherein the host cell is a prokaryotic cell.
14. The method according to any of the preceding items, wherein the host cell is *Escherichia coli*.
15. The method according to any of the preceding items, wherein the expression vector comprises a T7 promoter, a tac promoter, a lac promoter or the like.

DETAILED DESCRIPTION

The inventors have devised a simple method for optimising a sequence for protein expression in a host. By simultaneously generating a large number of sequence alterations on both sides of the triplet encoding the first codon, the method is capable of achieving surprisingly efficient expression of hard-to-express sequences, as evidenced by Example 2 and 3. The present invention therefore provides a solution to the problem of undesirably low expression levels of recombinant proteins. This is a common problem, and there is a long-felt need in the field for a simple, inexpensive and generally applicable solution.

Figure 8:
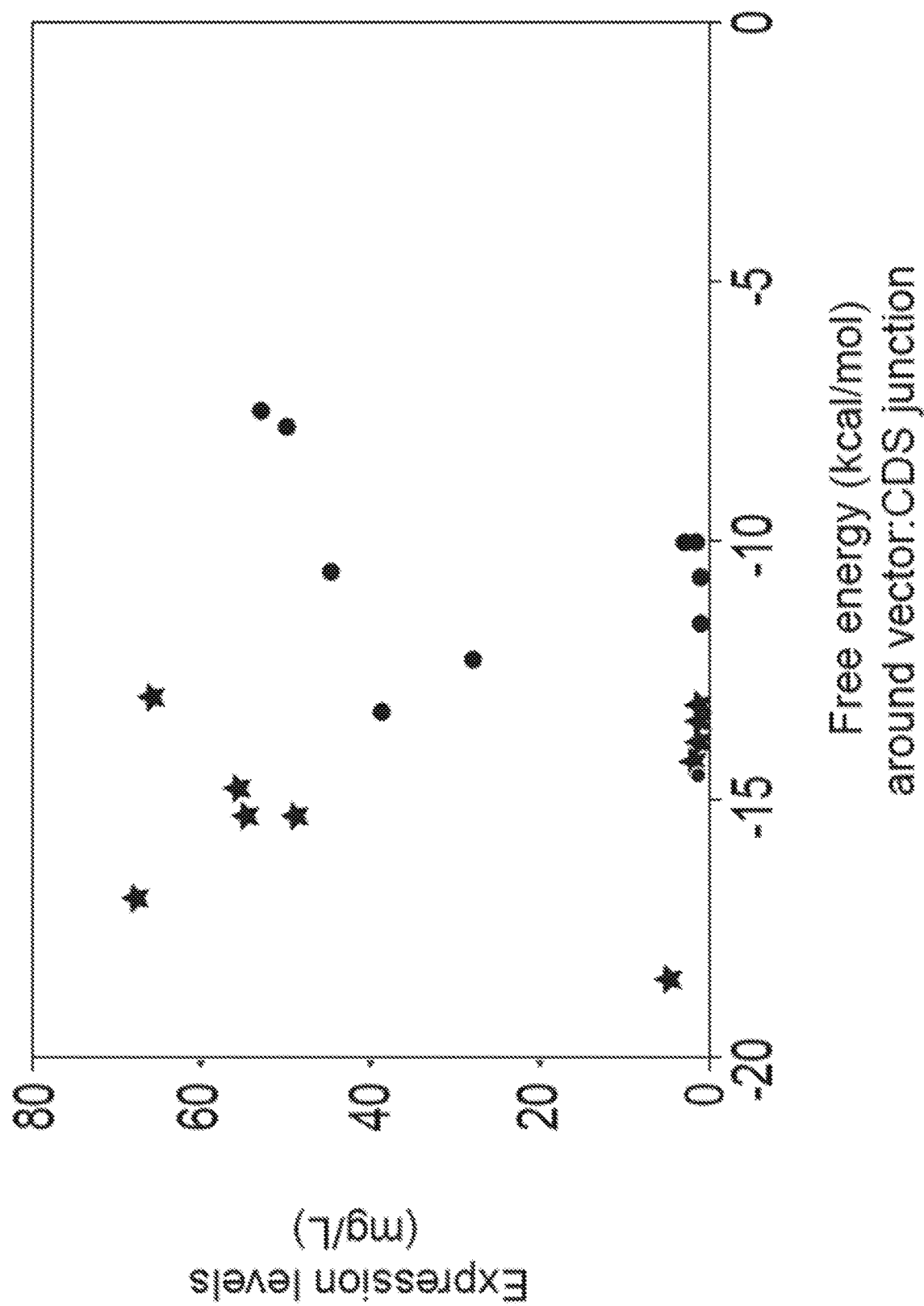
FIG. 8. mRNA structure of the vector:CDS junction does not explain differences in expression levels. Vector:CDS junctions from five highly expressed, and five poorly expressed clones from the pET28a$^{OPT}$-araH$^{OPT}$ and pET28a$^{OPT}$-narK$^{OPT}$ libraries were sequenced. $\Delta G$ values were calculated by analysing the nucleotide sequence around the AUG start codon (−20 to +37) with mFold and compared to the expression levels obtained. pET28a$^{OPT}$-araH$^{OPT}$ and pET28a$^{OPT}$-narK$^{OPT}$ are depicted as dots and stars respectively.

The molecular basis for the surprising efficiencies that can be obtained by the method of the invention has not been conclusively elucidated. However, it is important to note that the effects go beyond effects that would be expected from alterations in mRNA secondary structure in the region around the RBS. In fact the present results indicate that mRNA structure does not explain all of the variation in expression levels (FIG. 8). Without wishing to be bound by theory, the inventors believe that an optimal RBS contains three important variables; (1) relaxed mRNA structure, (2) a favourable nucleotide sequence for ribosome binding, and (3) optimal synonymous codons in the +2 and +3 positions, importance of which in combination has not been recognised earlier. By optimising the variables together, a synergistic improvement in translation efficiency can be obtained.

Figure 5:
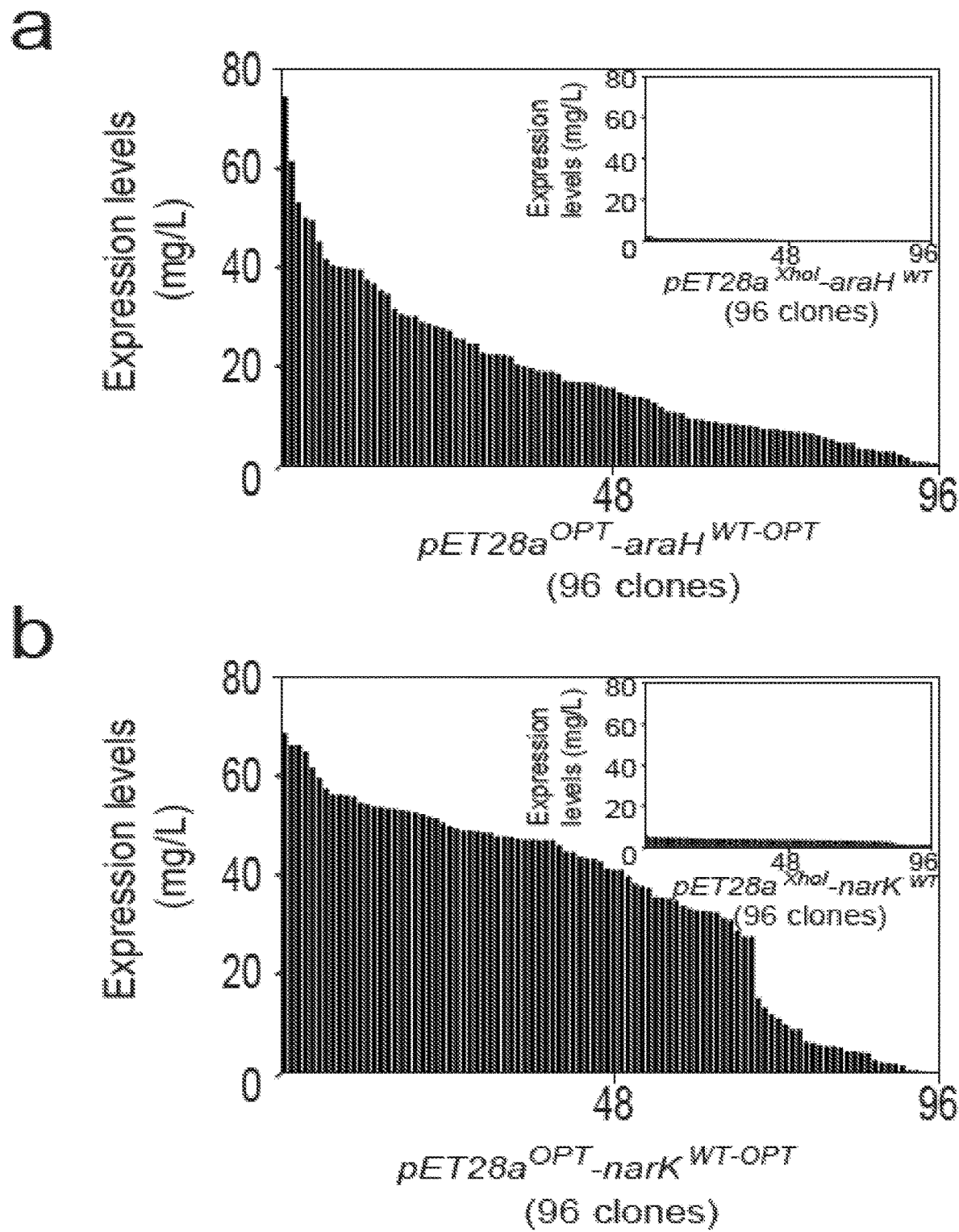
FIG. 5. Comparison of expression levels from 96 randomly selected clones in the pET28a$^{OPT}$-araH$^{WT-OPT}$ and pET28a$^{OPT}$-narK$^{WT-OPT}$ libraries (a and b, respectively). The clones were assayed as described in FIG. 3. The inset boxes show 96 randomly selected colonies of the original clone (or mother plasmid).
Figure 9:
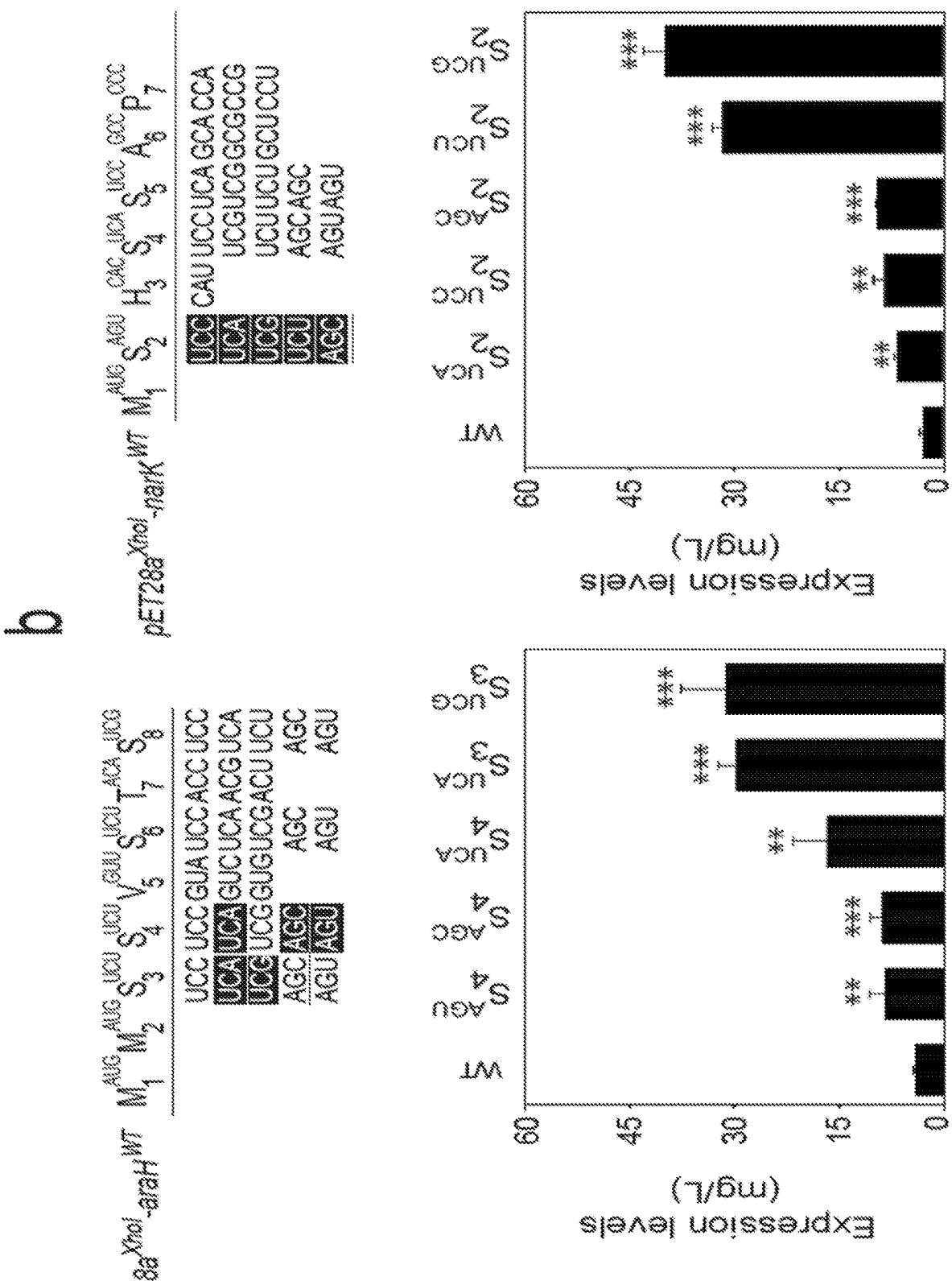
FIG. 9. Synonymous codon substitutions in the 5' coding sequence (CDS) of araH$^{WT}$ and narK$^{WT}$ affect expression. Previously we have shown that selective synonymous codon substitutions in the 5' CDS of araH$^{WT}$ and narK$^{WT}$ can increase expression levels[8] (see underlined residues). To explore this phenomenon in a systematic way we engineered all synonymous codons at the 5' end (one at a time) and monitored the effect on expression. (a) Top panel, the first eight amino acids of araH$^{WT}$ and the respective codons used are shown above the line. All possible synonymous codon substitutions were engineered and the CDSs were expressed as -TEV-GFP-His$_8$ fusions in the BL21(DE3)pLysS strain. Those codon substitutions that increased expression are boxed, and shown in the bottom panel. Error bars represent the standard deviation from three biological replicates. Statistical significance was determined by an unpaired two-tailed-Student's test assuming unequal variance. Three stars indicate a probability of P<0.001. Two stars indicate a probability of P<0.01. (b) As for (a) except that narK$^{WT}$ was used.

The inventors have extensively evaluated different synonymous codon variants at the 5' end of two different CDS (FIG. 9). The data shows that such approach was not able to achieve as high expression levels as the present invention (FIG. 5, compare expression levels with FIG. 9). Since the three variables above are currently very difficult to predict a priori, the best way to select an optimal RBS is to experimentally generate the library and screen for maximum expression (as provided by the method of the present disclosure).

The inventors also have benchmarked the present method against in silico prediction with mFold, a state-of-the-art predictor for mRNA stability. This predictor was not able to achieve the same high levels of expression as the present invention. The best clones predicted by mFold (FIG. 10) did not reach the expression levels of the best clones with the present invention (FIG. 5, compare levels of expression with those in FIG. 10).

Thus, the present invention relates to a method for optimising a nucleotide sequence for protein expression in a host cell, comprising the steps of:
   (a) constructing an expression library comprising a large number of variants of the sequence to be expressed operatively cloned in an expression vector, wherein
      (i) the sequence of the 6 nucleotides immediately upstream (5'-direction) of the triplet encoding the first codon of the coding sequence to be expressed is completely or partially randomized;
      (ii) the sequence encoding the second and third codons of the coding sequence to be expressed is randomized, wherein the randomization of the second and third codons is limited to changes not altering the amino-acids encoded by said codons;
   (b) screening the library with regard to efficiency of protein expression in the host cell; and
   (c) selecting a sequence resulting in a desired level of efficiency of protein expression.

If the 6 nucleotides in 5'-direction of the first codon of the sequence to be expressed are completely randomized, the library will contain $4^6=4096$ variants of said sequence element. Preferably, the 6 nucleotides in the 5'-direction of the first codon of the sequence to be expressed are completely randomized. While it is also possible to construct libraries where said 6 nucleotides are not completely randomized, this would result in a more or less limited optimisation.

It is contemplated that one, two, three, four or more of the 6 nucleotides might by design be chosen to be kept constant, and/or that one, two, three, four or more of the 6 nucleotides might by design be chosen to be randomised in a restricted manner. By randomisation in a restricted manner is meant that not all four potential alternatives are permitted in the design, i.e. the randomisation at a given position could be limited to 3 or 2 of the nucleotides available. As a hypothetical example merely for illustration, the nucleotide at position −1 could be randomised so that it is either A or G, position −2 could be constant C, the nucleotide at position −5 could be randomised to be either A, C or G and the remaining nucleotides fully randomized.

The library construction (e.g. by using degenerate primers) may be designed such that the library can be expected to contain at least 100, preferably at least 500, more preferably at least 1000, yet more preferably at least 2000, still more preferably at least 3000, highly preferably at least 4000, most preferably 4096 variants of the 6 nucleotides in 5'-direction of the first codon of the sequence to be expressed. It is to be understood that the library may not necessarily actually contain each possible sequence that it was designed for. Reasons may be purely stochastic or derive from difficult-to-predict phenomena relating to PCR efficiency, cloning efficiency or biological stability. Normally, the library will actually contain at least 80%, more at least preferably 90%, yet more preferably at least 95% of the sequences that it was designed to contain.

As apparent from the standard genetic code, certain amino-acids are encoded by up to 6 different codons, whereas other amino-acids only have a single codon. This is known as the degeneracy of the genetic code. For instance, the amino-acid leucine can be coded by 6 different codons (UUA, UUG, CUU, CUC, CUA and CUG), whereas methionine is only coded by AUG. Therefore, the degree of randomization available for the sequence of the second and third codons of the coding sequence varies from case to case. In one extreme, there is no room whatsoever for variation without changing the amino-acid sequence (e.g. if the second and the third amino-acids are a methionine and a tryptophan), in which case the present method would not be applicable. The present method requires that the library be designed to contain at least 2 variants of the sequence of the second and third codons. In the other extreme, if there the second and the third amino-acids are both leucine, there would be 6*6=36 available alternatives. Consequently, the library constructed by the method of the invention comprises at least 2, but preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 variants of the sequence of the second and third codons.

Thus, the theoretical maximum total number of variants in the library constructed by the method of the invention is 36*4096=147456. Preferably, a library constructed by the method of the invention contains at least 200, more preferably at least 1000, yet more preferably at least 4000, still more preferably at least 8000, even more preferably at least 10000 further more preferably at least 20000 variants of the nucleotide sequence to be optimised.

Library Construction

In the present context, the term "forward primer" is taken to mean a primer which comprises a sequence corresponding to the sequence of the sense strand of the coding sequence to be optimised. The "reverse primer" is taken to mean a primer comprising a sequence corresponding to the sequence of the antisense strand.

The construction step (a) may comprise a polymerase chain reaction (PCR) involving a set of degenerate forward nucleotide primers comprising:
(i) a sequence at least 6 completely or partially randomised nucleotides in 5'-direction of the first codon of the sequence to be expressed;
(ii) the sequence encoding the first codon of the sequence to be expressed (typically AUG); and
(iii) a partially randomized sequence of the second and third codons of the sequence to be expressed, wherein the randomization of the sequence of the second and third codons is limited to changes not altering the amino-acids encoded by said codons.

The library construction can also be performed using a corresponding set of degenerate reverse primers comprising the complement (antisense) sequence of the elements listed above. Needless to say, the elements are in that case in reverse order in the primers when read in the customary 5'->3' direction.

Assuming the forward primer is the degenerate primer, as a reverse primer, a suitable primer comprising a sequence corresponding to a suitable region towards the 3' end of the sequence to be cloned can be used. Alternatively, if the template being used in the PCR reaction is cloned in a vector, a reverse primer complementary to a suitable region of the vector can also be used.

If a degenerate reverse primer is used, a forward primer can be selected from a suitable location upstream of the translation initiation site, preferably such as to enable convenient cloning. Convenient cloning might entail that the PCR product contains restriction enzyme recognition sites allowing the product to be easily cloned into an expression vector containing the remaining elements needed for the expression library.

The sequence to be optimised is used as a template for the PCR reaction, and it can be provided in various different forms. Preferably, the template is a product of a previous PCR reaction, or a more or less purified vector (such as a plasmid, an artificial chromosome or a viral vector) in which the sequence to be optimised has been cloned. However, even chromosomal DNA of the organism from which the sequence to be optimised is originally defined could be used as a template.

Most preferably, the template is an expression vector in which the sequence to be optimised has been cloned. In this case, it is preferred that the 5' end of a set of degenerate forward primers is designed such that it matches the 5' end of a reverse primer (by e.g. about 15 nucleotides). Naturally, the corresponding approach can be performed by using a set of degenerate reverse primers and a forward primer. By this approach, the overlapping primers result in PCR products capable of circularising by homologous recombination and replicating when transformed into a suitable host such as *E. coli*, without need for additional in vitro manipulation. The template expression vector being derived from a biological source contains methylated nucleotides (as opposed from the PCR product that is unmethylated) and can be eliminated by digestion with a restriction enzyme only acting on methylated DNA, such as Dpnl. This method is generally known as whole-plasmid mutagenesis.

Alternatively, the PCR reaction products can be cloned in a conventional manner into a suitable expression vector, such as a vector of the pET series, pBAD or pDuet.

The PCR reaction can be performed in a conventional manner including mixing of the template, the primers, dNTPs, a thermostable polymerase such as Taq-polymerase or Pfu-polymerase in a suitable buffer to a reaction mixture, followed by thermal cycling of the reaction mixture. The thermal cycling will generally include repeated cycling at denaturation temperature, annealing temperature and an extension temperature (in some cases the annealing and extension temperatures may be the same). However, the specific conditions can be tailored to suit the individual circumstances. Ideally it is best to use an annealing temperature that is as low as possible, so that the highest possible proportion of the degenerate primers have a chance to participate in the PCR.

Besides PCR with degenerate primers, which is the preferred method for constructing the library, there are other known methods for site-specific mutagenesis that could in principle be utilized for the same purpose. One could construct the library of the invention by manufacturing a collection of synthetic genes differing from one another as specified herein. Alternatively, one could synthesize a collection of single-stranded oligonucleotides having the sequence alterations as specified herein. To the collection of oligonucleotides a primer could be annealed, and a primer extension reaction with a polymerase could be used to make or produce a collection of double-stranded molecules with the specified sequence alterations. Provided that the sequence of the template oligonucleotide is designed to contain suitable sites for restriction enzymes, the collection of double-stranded molecules could be easily cloned in an expression vector containing the remaining coding sequence and the remaining elements required for an expression library.

The meaning of "operative cloning" into an expression vector is defined as follows: operative cloning results in an expression vector with the cloned CDS that, when introduced into a suitable host under suitable conditions, induces expression of an mRNA molecule comprising at least the following features, in the following order from the 5' direction: (i) the sequence of the 6 nucleotides immediately upstream (5'-direction) of the first codon of the coding sequence to be expressed and (ii) the coding sequence to be expressed. In particular for prokaryotic hosts, the mRNA preferably comprises at least the following features, in the following order from the 5' direction: (i) a SD sequence (ii) the sequence of the 6 nucleotides immediately upstream (5'-direction) of the first codon of the coding sequence to be expressed and (iii) the coding sequence to be expressed.

Preferably, the expression vector sequence comprises a SD sequence. However it is also possible to include this SD in the primer(s).

Preferably, the expression vector comprises features resulting in expression of a fusion protein, with the coding sequence to be expressed and a detectable marker known in the art, such as green fluorescent protein (GFP), yellow fluorescent protein (YFP), red fluorescent protein (RFP) or the like.

Preferably, the expression vector is a high copy number vector in order to maximise the level of expression. Preferably, the expression vector comprises a T7 promoter.

However, the method should be equally applicable to any expression vector having any copy number and/or using any type of promoter. Since the method aims to optimise the translation initiation, the relative increase in expression level is independent of the type of promoter or the copy number of the vector.

Screening and Selection

Preferably, the host cell is a prokaryotic cell. Most preferably, the host cell is an *Escherichia coli* cell. However, the method may also be applied to expression in a eukaryotic host, where the region around the first codon (known as the Kozak sequence) also affects the translation efficiency.

In the screening step, individual clones from the library are randomly selected for analysis of the protein expression level. In most cases, analysis of about 100 individual clones gives a fair indication of the expression levels achievable with the method. The individual clones are cultured in similar conditions (that are suitable for expression) and the level of protein expression determined for each individual clone.

The determination of the level of expression is greatly simplified if the library is constructed such that the coding sequence is expressed as a fusion protein with a detectable marker such as GFP or a similar fluorescent protein. This allows convenient determination of the expression level using e.g. whole cell fluorescence, flow cytometry or in-gel fluorescence. However, any method of analysing the level of protein expression can be used, such as SDS-PAGE, Western blot, mass spectrometry, ELISA or other immunochemical methods and the like.

When a clone having a desired (high) expression level is discovered, it is selected for further studies.

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be interpreted as limiting the scope of the invention. For experimental details pertaining to the examples below, the skilled reader is directed to the separate Materials and Methods section below.

Example 1: Serendipitous Improvements in Expression Efficiency

Figure 2:
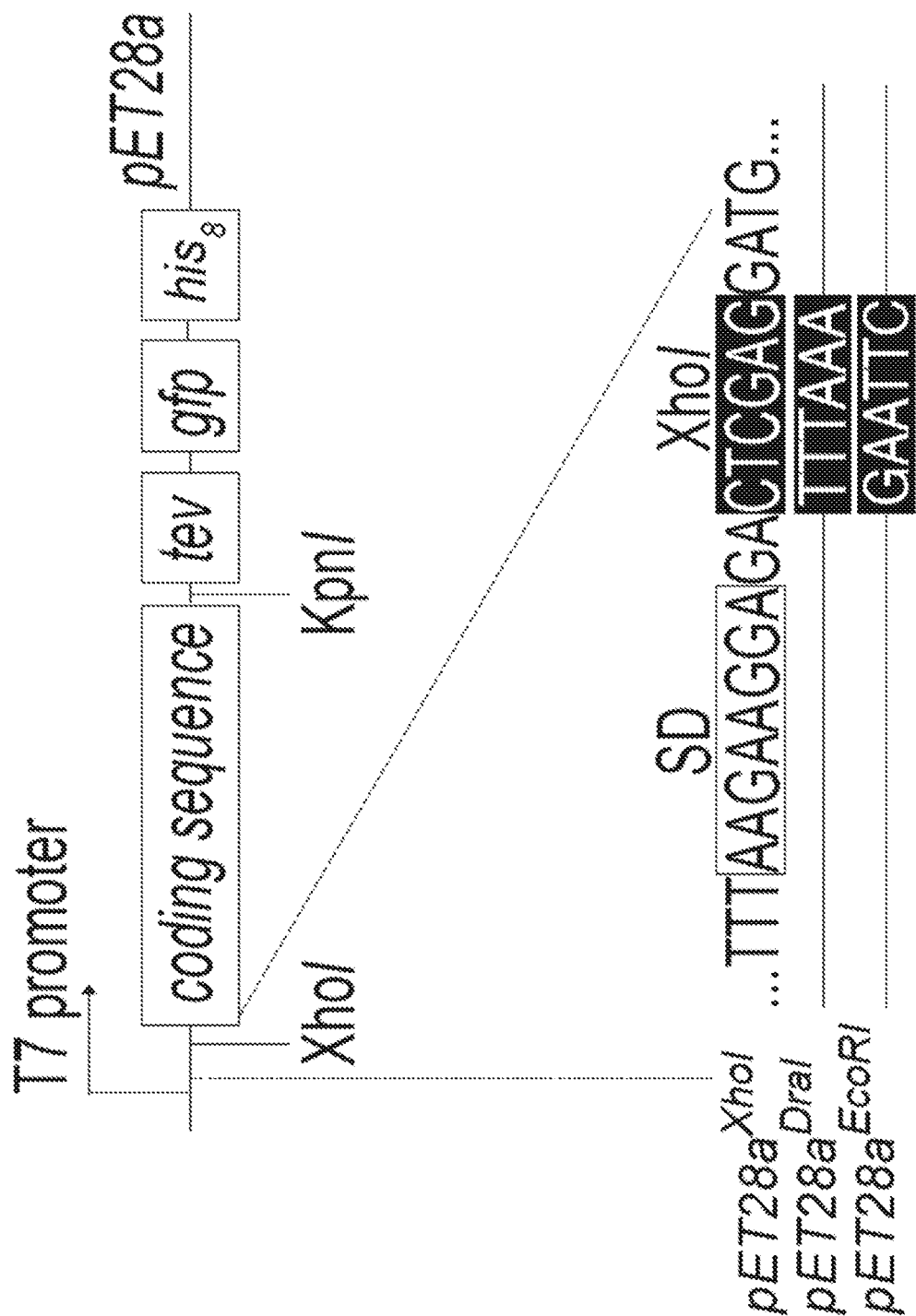
FIG. 2. Overview of the expression cassette used. CDSs were cloned into a derivative of the pET28a vector (called pET28a$^{XhoI}$ here and pGFPe elsewhere[10]) using XhoI and KpnI restriction endonucleases. They were genetically fused to a region encoding the tobacco etch virus protease recognition sequence (TEV), the green fluorescent protein (GFP) and an octa-histidine purification tag (His$_8$). In some experiments, the original XhoI site, located between the Shine-Dalgarno sequence (SD) and the AUG start codon, was changed to DraI or EcoRI. Refer to SEQ ID NO: 2.
Figure 3:
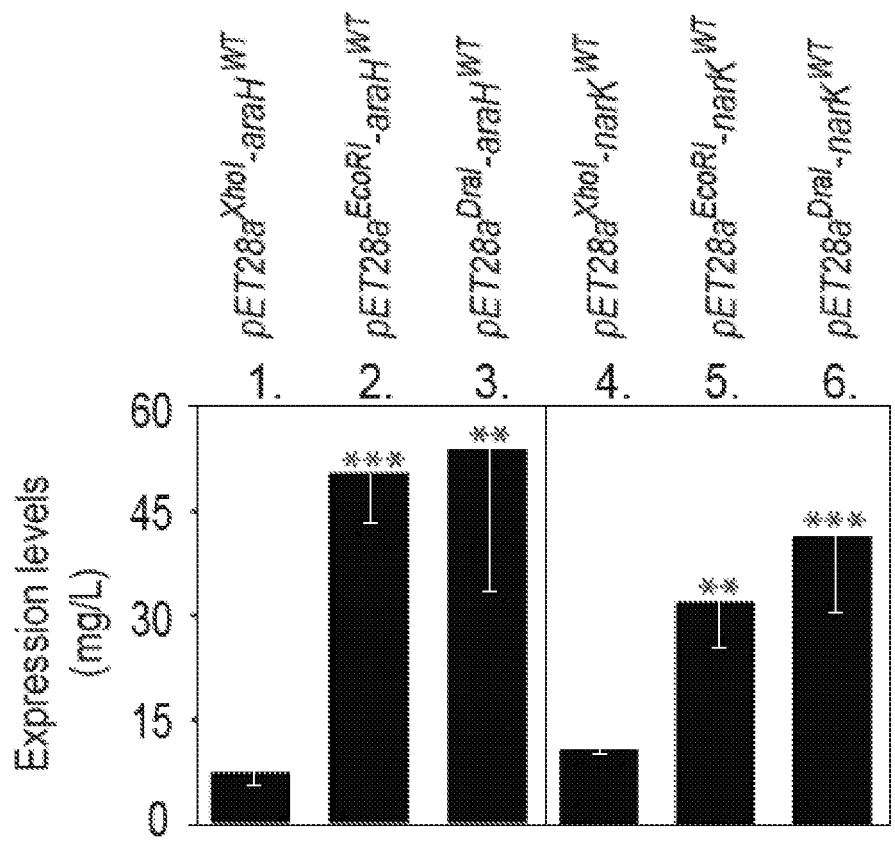
FIG. 3. Comparison of expression levels for araH$^{WT}$ and narK$^{WT}$ when expressed from the original vector (pET28a$^{XhoI}$) or vectors where the 5' XhoI site was changed (pET28a$^{DraI}$ or pET28a$^{EcoRI}$). (a) The constructs were transformed into the BL21(DE3)pLysS strain and expression was induced with 1.0 mM IPTG for 5 hours at 25° C. To estimate the amount of protein produced in mg/L, we compared the whole cell fluorescence values to a standard curve obtained with free GFP. These estimates were not influenced by free GFP, as we only detected full-length fusion proteins when we analysed cellular extracts by Western blotting and in-gel fluorescence. Error bars represent the standard deviation from three biological replicates. Statistical significance was determined by an unpaired two-tailed-Student's test assuming unequal variance. Three stars indicate a probability of P<0.001. Two stars indicate a probability of P<0.01. (b) Prediction of mRNA stability around the AUG start codon (i.e. −20 to +37). The free energy ($\Delta G$) associated with mRNA folding was calculated in kcal/mol using mFold, and plotted against the expression level. Numbers correspond to clones described in b.
Figure 3:
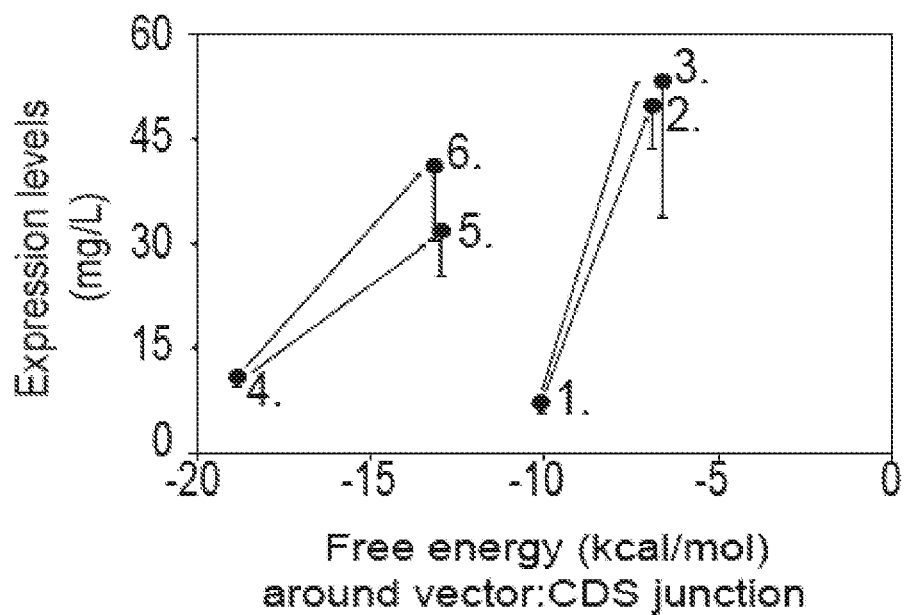

Previously we constructed a clone library encoding 501 *E. coli* inner membrane proteins genetically fused to a -TEV-GFP-His$_8$ tag[10]. During construction of the library, the CDSs had been cloned into a modified version of the pET28a vector (herein called pET28a$^{XhoI}$), using 5' XhoI and 3' KpnI restriction endonucleases (FIG. 2). The clones were transformed into the BL21(DE3)pLysS strain and expression levels were compared by whole cell fluorescence[10]. This experiment indicated that a number of CDSs were difficult-to-express, including araH$^{WT}$ and narK$^{WT}$. araH$^{WT}$ encodes for the membrane component of the arabinose ABC transporter, and narK$^{WT}$ a nitrate/nitrite antiporter of the major facilitator superfamily. Whilst working with these two CDSs we noted that substituting the 5' XhoI recognition sequence in pET28a$^{XhoI}$ to either EcoRI or DraI dramatically increased the level of expression (FIG. 3a). The most likely explanation for this observation is that the combination of XhoI recognition sequence and the 5' end of the araH$^{WT}$/narK$^{WT}$ resulted in a vector:sequence junction that was prone to form stable secondary structures when transcribed into mRNA, and that changing the restriction site relaxed these structures. Analysis of mRNA stability encoded in the vector:CDS junction supported this hypothesis (FIG. 3b).

Example 2: Systematic Optimisation of the Vector:CDS Junction of the RBS

Figure 4:
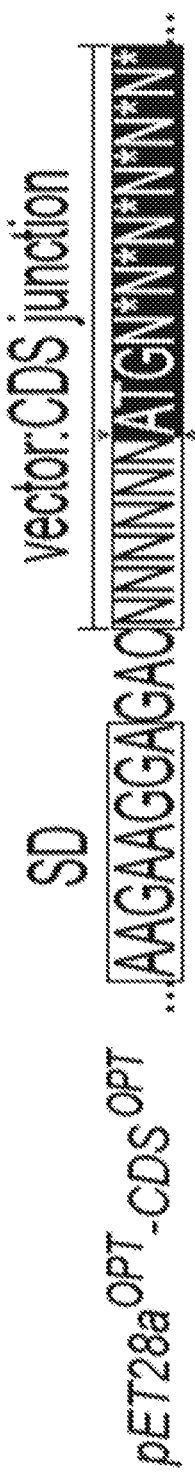
FIG. 4. An overview of the random mutagenesis approach that generated libraries of vector:CDS junctions. Randomisation of the six nucleotides upstream of the ATG allowed all possible nucleotides (denoted N), whilst the six nucleotides downstream were restricted to nucleotides that did not change the sequence of the encoded protein (denoted N*). Refer to SEQ ID NO: 3.
Figure 6:
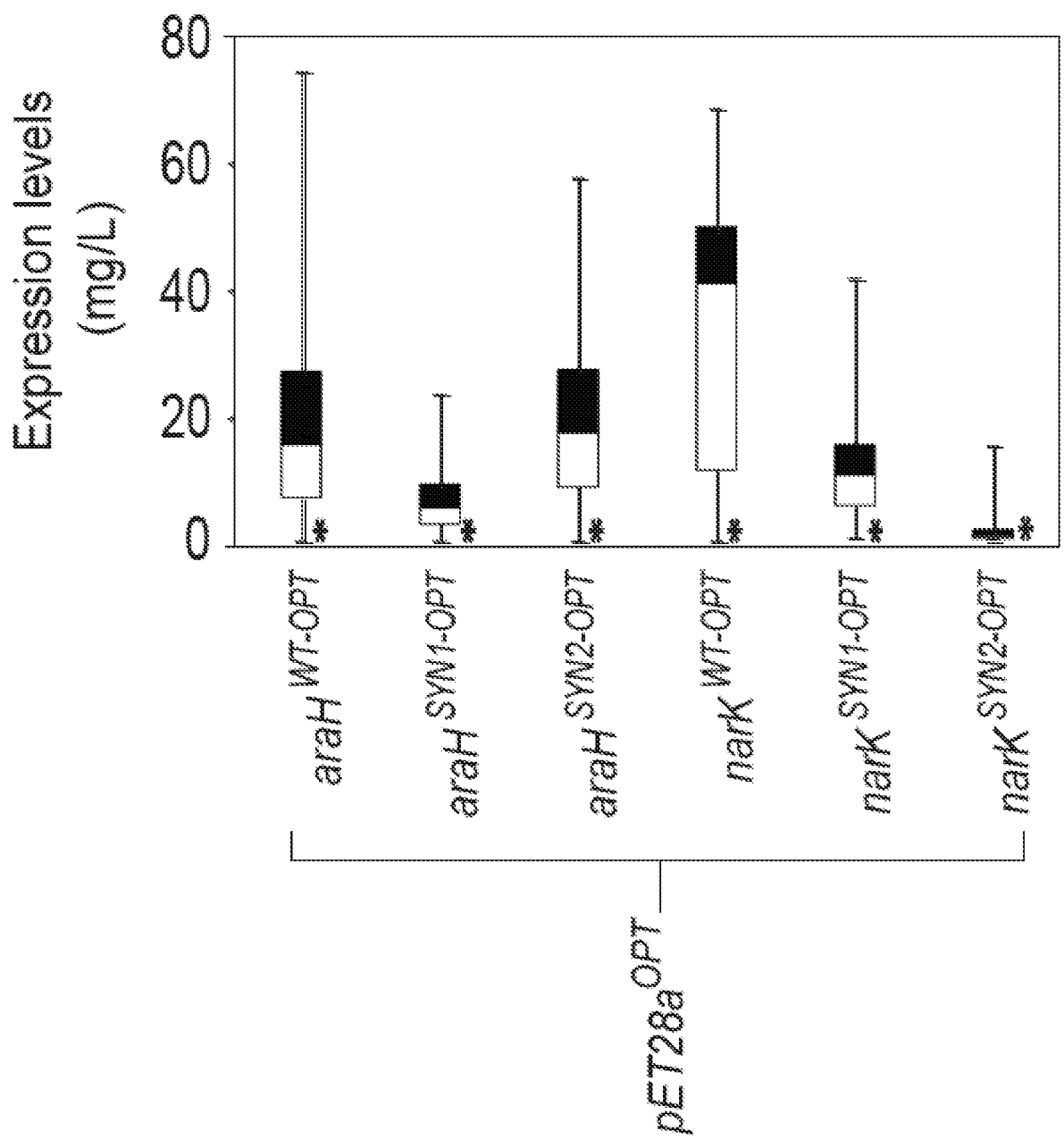
FIG. 6. Box and whisker plot showing the differences in expression from 96 clones in the pET28a$^{OPT}$-araH$^{WT-OPT}$ and pET28a$^{OPT}$-narK$^{WT-OPT}$ libraries, as well as libraries generated with synthetic versions of each CDS that had been optimised by commercial vendors[8]. The top and bottom ends of the line represent the highest and lowest expression levels observed. Expression levels of the original (i.e. un-optimised) clone are marked with an asterisk (*).

To select the nucleotide composition at the vector:CDS junction in a systematic way, we generated libraries in vitro by PCR using degenerate primers. In this experiment the six nucleotides upstream of the AUG start codon were changed in all possible combinations whilst the six downstream were limited to synonymous codons (FIG. 4). The libraries, called pET28a$^{OPT}$-araH$^{OPT}$ and pET28a$^{OPT}$-narK$^{OPT}$, thus contained up to 24,576 and 49,152 different vector:CDS junctions respectively. Each library was transformed into the BL21(DE3)pLysS strain and expression levels from 96 randomly selected colonies were monitored, as done earlier. We observed a range of expression levels, which differed by approximately 350-fold (i.e. lowest to highest expression; FIG. 5). Two lines of evidence indicated that the differences in expression were caused by differences in vector:CDS junctions, not cell-to-cell variation. (1) Sequencing of five highly-expressed and five poorly-expressed clones indicated that the vector:CDS junction was always different, and (2) little variation was observed when we assayed 96 colonies of the original (i.e. un-optimised) pET28a$^{XhoI}$-araH$^{WT}$ and pET28a$^{XhoI}$-narK$^{WT}$ clones (see inset FIG. 5). Notably, the highest expressing clones from our relatively small-scale screen were in excess of 60 mg/L for both pET28a$^{OPT}$-araH$^{OPT}$ and pET28a$^{OPT}$-narK$^{OPT}$. This level of expression is suitable for any application, however it could be increased if more junctions were sampled using fluorescence activated cell sorting. Interestingly, the expression levels could not be further increased using coding sequences that had been optimised by commercial vendors (FIG. 6). This observation emphasises the influence of the vector:CDS on expression levels, and the importance of post-cloning optimisation.

Significantly, the differences in expression that we observed by post-cloning optimisation of the vector:CDS junction could not be explained by mRNA structure alone, as there was no correlation between ΔG values and expression levels when we analysed the vector:CDS junctions from five highly-expressed and five poorly-expressed sequences in the pET28a$^{OPT}$-araH$^{OPT}$ and pET28a$^{OPT}$-narK$^{OPT}$ libraries (FIG. 8). This is most likely because the libraries sampled six nucleotides downstream of the AUG start codon and therefore synonymous codon choice in the +2 and +3 positions (in addition to mRNA structure). Synonymous codon choice in these positions can affect expression of araH$^{WT}$ and narK$^{WT}$ ([8] and FIG. 9) as well as other CDSs[9] and is therefore an important variable in its own right.

Figure 10:
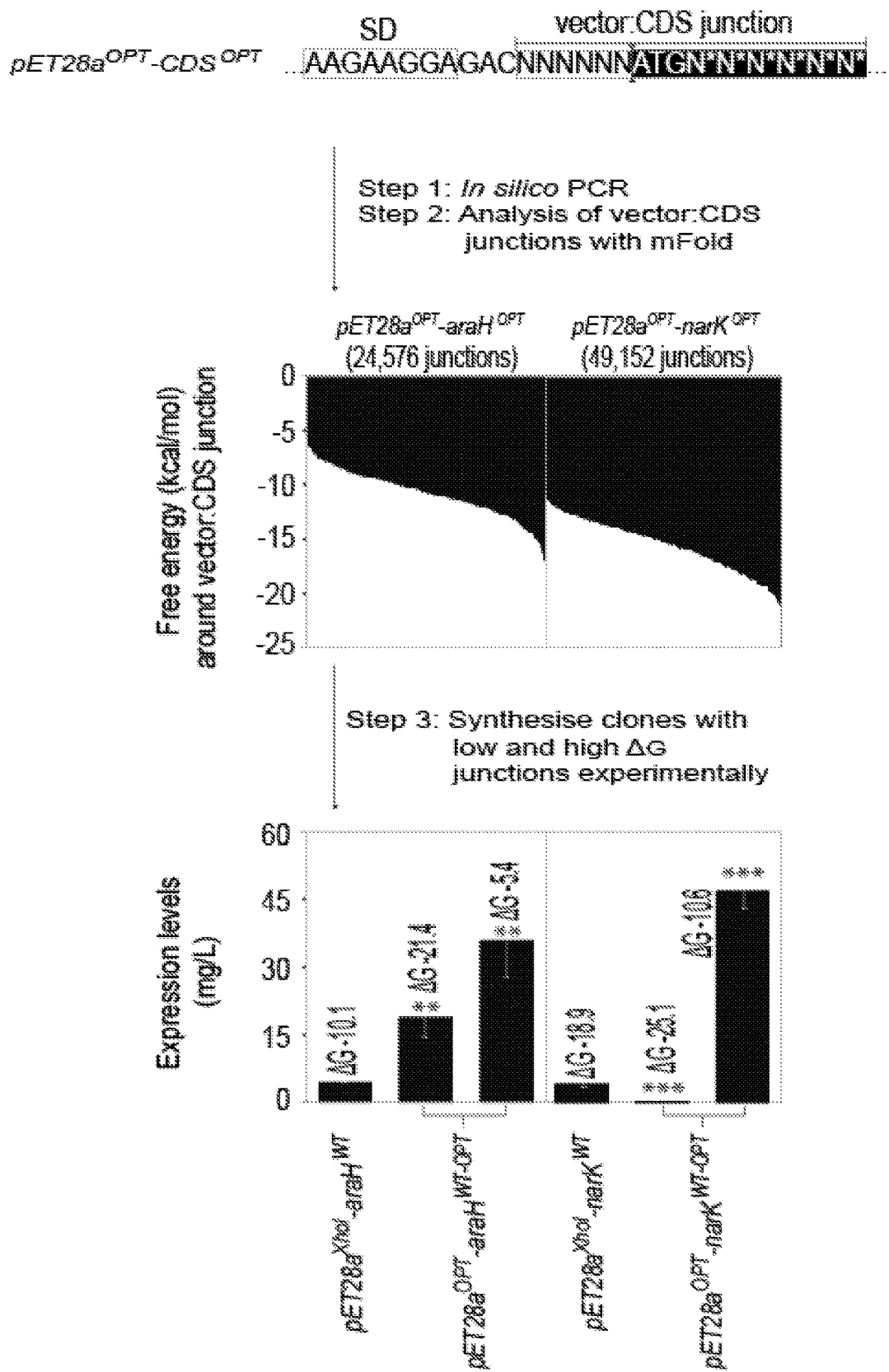
FIG. 10. Prediction of optimal vector:CDS junctions by in silico PCR and analysis of mRNA structure. An overview of the in silico mutagenesis that generated libraries of vector: CDS junctions. Randomisation of the six nucleotides upstream of the ATG allowed all possible nucleotides (denoted N), whilst the six nucleotides downstream were restricted to nucleotides that did not change the sequence of the encoded protein (denoted N*). mRNA structure encoded in the vector:CDS junction (i.e. nucleotides −20 to +37) was then analysed using mFold, and $\Delta G$ values were ranked from high to low (top box). The vector:CDS junction with the highest and lowest $\Delta G$ were engineered, and the levels of expression compared. Error bars represent the standard deviation from three biological replicates. Statistical significance was determined by an unpaired two-tailed-Student's test assuming unequal variance. Three stars indicate a probability of P<0.001. Two stars indicate a probability of P<0.01. Note that expression level does not always correlate with $\Delta G$ value.

Despite the fact that differences in expression did not correlate with mRNA structure alone, a relaxed mRNA structure could be used as a rough guide to pick a vector:CDS junction ab initio. For example, when we generated the pET28a$^{OPT}$-araH$^{OPT}$ and pET28a$^{OPT}$-narK$^{OPT}$ libraries in silico and selected sequences using mFold we could identify vector:CDS junctions that expressed reasonably well (FIG. 10). However, since a relaxed mRNA structure at the vector:CDS junction is necessary, but not sufficient for efficient expression it is unlikely that maximum expression could be reached using this approach. The most effective way to optimise a vector:CDS junction is therefore to experimentally generate libraries and screen for well expressing clones.

Example 3: General Applicability of the Optimisation Method

Figure 7:
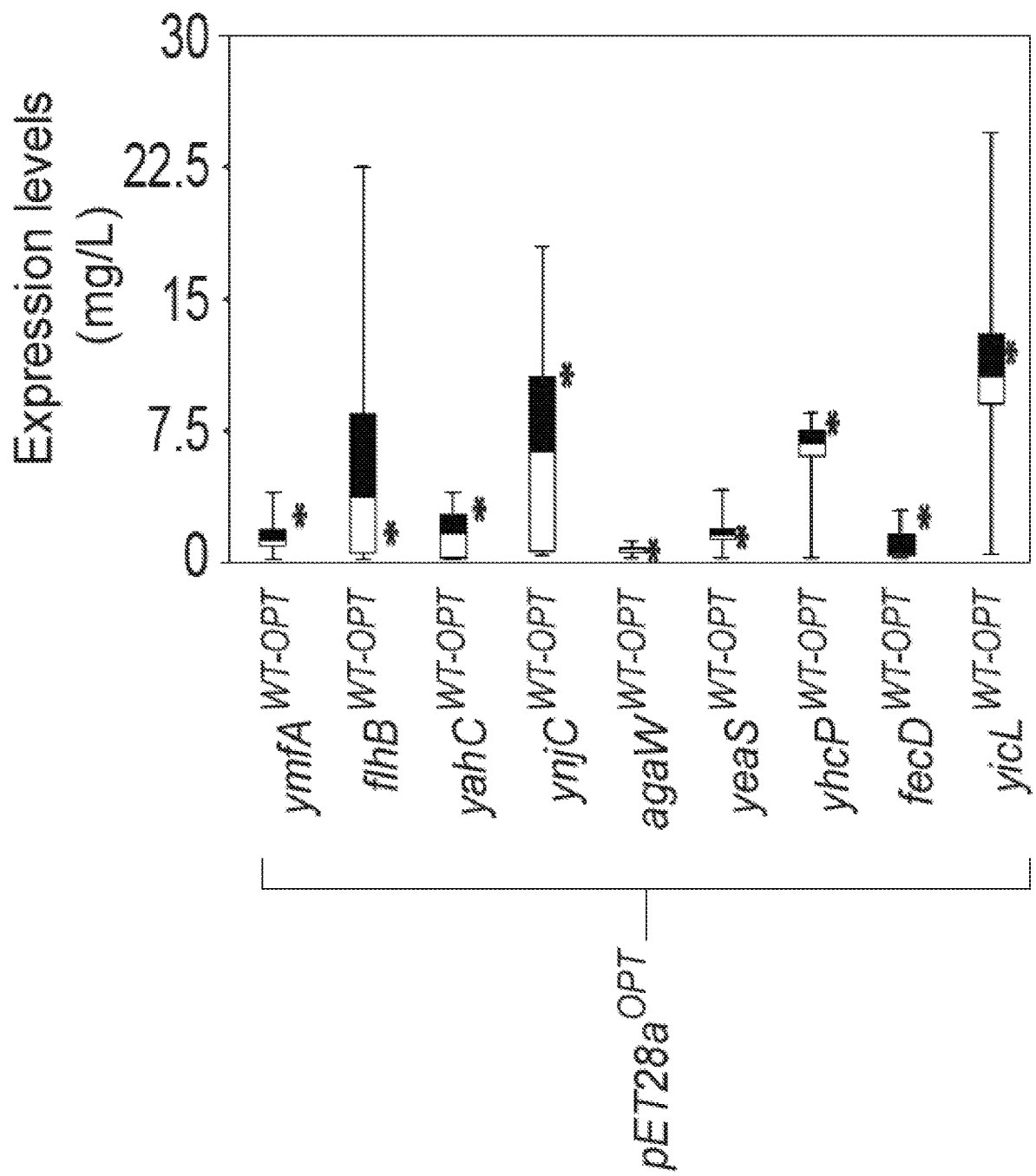
FIG. 7. As for FIG. 6 except that the libraries were generated from nine additional CDSs in a previously synthesised library[10]. These CDS all encode E. coli membrane proteins.

The importance and generality of optimisation of the vector:CDS junction was exemplified using an additional nine random clones from our membrane protein-TEV-GFP-His library[10]. We always observed a range of expression levels when we created libraries of vector:CDS junctions, ranging from 280-fold (pET28$^{OPT}$-flhB$^{OPT}$) to 7 fold (pET28$^{OPT}$-agaW$^{OPT}$) (FIG. 7). In all cases we could increase expression relative to the original and un-optimised clone. Some of these un-optimised clones were originally difficult-to-express, whilst others originally expressed to reasonable levels.

Materials and Methods
Molecular Cloning

All coding sequences (CDSs) were harboured in a vector derived from pET28a (also called pGFPe), as previously described[10]. They were genetically fused at the 3' end to a sequence that encoded the tobacco-etch virus (-TEV-) protease recognition site, the green fluorescent protein (-GFP-) and an octa histidine purification tag (-His$_8$). Site-directed mutagenesis was performed using the QuickChange Site-Directed Mutagenesis Kit (Stratagene) and constructs were verified by DNA sequencing (Eurofins MWG operon, Germany).

Libraries of different vector:CDS junctions were amplified from the original clone[10] using a reverse primer located in the pET28a$^{XhoI}$ vector (5'-TCTCCTTCTTAAAGT-TAAACAAAATTATTCTAGAGGGGAATTGTTATCCG-3') (SEQ ID NO: 1) and a degenerate forward primer. The forward primer followed the following design principles: (1) The six nucleotides upstream of the AUG start codon were changed in all possible combinations. (2) The six nucleotides downstream of the AUG start codon were changed in combinations that allowed for all synonymous codon substitutions. (3) The primers extended to regions flanking the mismatched area. These regions were 16-23 nucleotides on either side and they matched the target sequence. (4) The 5' end of the forward primer matched the 5' end of the reverse primer (15 nucleotides), so that the PCR products could circularise by homologous recombination when transformed into E. coli. Note that in some cases it was not possible to design a single forward primer, so two primers were used and PCR products were mixed. Amplification by PCR was carried out using the Q5 polymerase (New England Bio-Labs) in a program that consisted of: 95° C. for 2 minutes, then 30 cycles of 95° C. for 45 seconds/48-68° C. for 45 seconds (using a gradient block), 72° C. for 6.5 minutes, and 68° C. for 12 minutes. Forty units of DpnI were added to 20 μL of the PCR product, and it was then transformed into the E. coli strain MC1061 (to facilitate circularisation). The transformation was transferred to 100 mL of Luria-Bertani (LB) media containing 50 μg/ml kanamycin and 34 μg/ml chloramphenicol and incubated at 37° C. with shaking for 16 hours. Purification of the plasmid library was carried out using the ENZA DNA mini kit I. To ensure that there was significant diversity in the library, we plated out a small aliquot and sequenced five random colonies. In every case, we received five different sequences.

Expression

Plasmids and plasmid libraries were transformed into BL21(DE3)pLysS using standard protocols. Overnight cultures were prepared by inoculating a single colony in 800 μl of LB liquid media containing 50 μg/ml kanamycin and 34 μg/ml chloramphenicol. Cultures were incubated in a 2.2 ml 96-well plate and incubated at 37° C. with shaking for 16 hours. Cultures were then back-diluted (1:50) into 5 ml of LB plus antibiotics in a 24-well growth plate, and incubated as before until an OD$_{600}$ of approximately 0.3 was reached. Expression was induced by addition of 1 mM isopropyl-b-D-thiogalactopyranoside (IPTG) and incubation for 5 hours at 25° C. with shaking. The $OD_{600}$ was measured and cells were harvested by centrifugation at 4000×g for 10 min, then resuspended in 1 mL of GFP resuspension buffer [50 mM Tris-HCl pH 8.0, 200 mM NaCl, 15 mM EDTA] and transferred to a 96-well optical bottom plate. Fluorescence was read in a Spectramax Gemini (Molecular Devices) at an excitation wavelength of 485 nm and an emission wavelength of 513 nm. The amount of GFP produced (in mg/L) was calculated using a standard curve obtained from purified GFP mixed with whole cells (to account for quenching). When libraries were assayed, the five most highly expressed and five most poorly expressed clones were sequenced to ensure that there was diversity in the experiment. In every case, we received ten different sequences.

Free Energy Measurements

The free energy (ΔG) associated with mRNA folding was calculated in kcal/mol using mFold with default settings in a window from −20 through to +37 relative to the A of the AUG start codon.

REFERENCES

1. Mutalik, V. K. et al. Quantitative estimation of activity and quality for collections of functional genetic elements. Nature methods 10, 347-353 (2013).
2. Salis, H. M., Mirsky, E. A. & Voigt, C. A. Automated design of synthetic ribosome binding sites to control protein expression. Nature biotechnology 27, 946-950 (2009).
3. Dvir, S. et al. Deciphering the rules by which 5'-UTR sequences affect protein expression in yeast. Proceedings of the National Academy of Sciences of the United States of America 110, E2792-2801 (2013).
4. Hui, A., Hayflick, J., Dinkelspiel, K. & de Boer, H. A. Mutagenesis of the three bases preceding the start codon of the beta-galactosidase mRNA and its effect on translation in *Escherichia coli*. The EMBO journal 3, 623-629 (1984).
5. Cheong, D. E. et al. Enhancing Functional Expression of Heterologous Proteins Through Random Substitution of Genetic Codes in the 5' Coding Region. Biotechnology and bioengineering (2014).
6. Kudla, G., Murray, A. W., Tollervey, D. & Plotkin, J. B. Coding-sequence determinants of gene expression in *Escherichia coli*. Science 324, 255-258 (2009).
7. Looman, A. C. et al. Influence of the codon following the AUG initiation codon on the expression of a modified lacZ gene in *Escherichia coli*. The EMBO journal 6, 2489-2492 (1987).
8. Norholm, M. H. et al. Improved production of membrane proteins in *Escherichia coli* by selective codon substitutions. FEBS letters 587, 2352-2358 (2013).
9. Stenstrom, C. M., Jin, H., Major, L. L., Tate, W. P. & Isaksson, L. A. Codon bias at the 3'-side of the initiation codon is correlated with translation initiation efficiency in *Escherichia coli*. Gene 263, 273-284 (2001).
10. Daley, D. O. et al. Global topology analysis of the *Escherichia coli* inner membrane proteome. Science 308, 1321-1323 (2005).

The invention claimed is:

1. A method for optimising a nucleotide sequence for protein expression in a host cell comprising:
   constructing an expression library comprising a plurality of variants of a coding sequence to be expressed, wherein individual members of the plurality are operatively cloned in an expression vector, wherein
   i. a sequence of 6 nucleotides immediately upstream in the 5' direction of the sequence of a first codon of the coding sequence to be expressed is completely randomized;
   ii. sequences of a second codon and a third codon of the coding sequence to be expressed are randomized, wherein the randomization of the second and third codons results in changes that do not alter the amino-acids encoded by said second and third codons;
   screening the expression library to determine efficiency of protein expression in the host cell; and
   selecting an optimized nucleotide sequence that results in a desired level of efficiency of protein expression.

2. The method according to claim 1, wherein constructing the expression library comprises conducting a PCR reaction using a set of degenerate primers comprising:
   (i) a sequence of least 6 completely randomised nucleotides immediately upstream in the 5'-direction of the first codon of the coding sequence to be expressed;
   (ii) the sequence encoding the first codon of the coding sequence to be expressed; and
   (iii) a randomized sequence of the second and third codons of the coding sequence to be expressed, wherein the randomization of the sequence of the second and third codons results in changes that do not alter the amino-acids encoded by said second and third codons;
   or the complement of said sequences in (i)-(iii).

3. The method according to claim 1, wherein the library comprises at least 1000 variants of the 6 nucleotides immediately upstream in the 5'-direction of the first codon of the sequence to be expressed.

4. The method according to claim 1, wherein the library comprises at least 2 variants of the sequence of the second and third codons.

5. The method according to claim 1, wherein the library comprises at least 4000 variants of the nucleotide sequence to be optimised.

6. The method according to claim 1, wherein the operative cloning in the expression vector results, when the expression vector is introduced into a suitable host cell under suitable conditions, in expression of an mRNA molecule comprising at least the following features, in the following order from the 5' direction: (i) the sequence of the 6 nucleotides immediately upstream in the 5'-direction of the first codon of the coding sequence to be expressed and (ii) the coding sequence to be expressed.

7. The method according to claim 1, wherein the operative cloning in the expression vector results, when the expression vector is introduced into a suitable host cell under suitable conditions, in expression of an mRNA molecule comprising at least the following features, in the following order from the 5' direction: (i) a Shine-Dalgarno sequence; (ii) the sequence of the 6 nucleotides immediately upstream in the 5'-direction of the first codon of the coding sequence to be expressed; and (iii) the coding sequence to be expressed.

8. The method according to claim 1, wherein the library is constructed such that the sequence to be expressed is expressed as a fusion protein with a detectable marker.

9. The method according to claim 8, wherein the detectable marker is a fluorescent protein.

10. The method according to claim 9, wherein the screening is performed by flow cytometry.

11. The method according to claim 1, wherein the expression vector comprises a Shine-Dalgarno sequence.

12. The method according to claim 1, wherein the expression vector is a high copy number vector.

13. The method according to claim 1, wherein the host cell is a prokaryotic cell.

14. The method according to claim 1, wherein the host cell is *Escherichia coli*.

15. The method according to claim 1, wherein the expression vector comprises a T7 promoter, a tac promoter, or a lac promoter.

16. The method according to claim 2, wherein the library comprises at least 1000 variants of the 6 nucleotides immediately upstream in the 5'-direction of the first codon of the sequence to be expressed.

17. The method according to claim 2, wherein the library comprises at least 2 variants of the sequence of the second and third codons.

18. The method according to claim 2, wherein the library comprises at least 4000 variants of the nucleotide sequence to be optimised.

19. The method according to claim 2, wherein the operative cloning in the expression vector results, when the expression vector is introduced into a suitable host cell under suitable conditions, in expression of an mRNA molecule comprising at least the following features, in the following order from the 5' direction: (i) the sequence of the 6 nucleotides immediately upstream in the 5'-direction of the first codon of the coding sequence to be expressed and (ii) the coding sequence to be expressed.

20. The method according to claim 2, wherein the operative cloning in the expression vector results, when the expression vector is introduced into a suitable host cell under suitable conditions, in expression of an mRNA molecule comprising at least the following features, in the following order from the 5' direction: (i) a Shine-Dalgarno sequence; (ii) the sequence of the 6 nucleotides immediately upstream in the 5'-direction of the first codon of the coding sequence to be expressed; and (iii) the coding sequence to be expressed.

21. The method according to claim 2, wherein the library is constructed such that the sequence to be expressed is expressed as a fusion protein with a detectable marker.

22. The method according to claim 21, wherein the detectable marker is a fluorescent protein.

23. The method according to claim 16, wherein the library is designed to comprise at least 2 variants of the sequence of the second and third codons.

24. The method according to claim 16, wherein the library comprises at least 4000 variants of the nucleotide sequence to be optimised.

25. The method according to claim 23, wherein the library comprises at least 4000 variants of the nucleotide sequence to be optimised.

26. The method according to claim 3, wherein the library comprises at least 2 variants of the sequence of the second and third codons.

27. The method according to claim 3, wherein the library comprises at least 4000 variants of the nucleotide sequence to be optimised.

28. The method according to claim 27, wherein the library comprises at least 4000 variants of the nucleotide sequence to be optimised.

29. The method according to claim 28, wherein the library is constructed such that the sequence to be expressed is expressed as a fusion protein with a detectable marker.

30. The method according to claim 29, wherein the detectable marker is a fluorescent protein.

\* \* \* \* \*